US00PP29109P2

(12) United States Plant Patent
Blom

(10) Patent No.: US PP29,109 P2
(45) Date of Patent: Mar. 13, 2018

(54) ***ASTER* PLANT NAMED 'X BLUE'**

(50) Latin Name: *Aster alpinus*
Varietal Denomination: X Blue

(71) Applicant: Arie Blom, Vleuten (NL)

(72) Inventor: Arie Blom, Vleuten (NL)

( * ) Notice: Subject to any disclaimer, the term of this patent is extended or adjusted under 35 U.S.C. 154(b) by 15 days.

(21) Appl. No.: 14/999,174

(22) Filed: Apr. 7, 2016

(51) Int. Cl.
*A01H 5/02* (2006.01)

(52) U.S. Cl.
USPC ..... Plt./355

(58) Field of Classification Search
USPC ..... Plt./355

CPC ..... A01H 5/025; A01H 5/02; A01H 5/0227; A01H 5/00
See application file for complete search history.

(56) References Cited

PUBLICATIONS

CNB New Plants catalogue retrieved on Jun. 21, 2017, retrieved from the Internet at <http://www.cnb.nl/EN/Pages/Product-Catalog.aspx?ProductId=232> one page.*

* cited by examiner

*Primary Examiner* — June Hwu
(74) *Attorney, Agent, or Firm* — Penny J. Aguirre

(57) ABSTRACT

A new cultivar of *Aster* named 'X Blue' that is characterized by its inflorescences that are fully double and purple-blue in color, and it's freely branching and compact plant habit.

2 Drawing Sheets

Botanical classification: *Aster alpinus.*
Variety denomination: 'X Blue'.

CROSS REFERENCE TO A RELATED APPLICATION

This application is co-pending with U.S. Plant Patent Applications filed for plants derived from the same breeding program that are entitled *Aster* Plant Named 'X Pink' (U.S. Plant patent application Ser. No. 14/999,173) and *Aster* Plant Named 'X White' (U.S. Plant patent application Ser. No. 14/999,175).

BACKGROUND OF THE INVENTION

The present invention relates to a new and distinct cultivar of *Aster alpinus*, botanically known as *Aster* 'X Blue', and will be referred to hereafter by its cultivar name, 'X Blue'. 'X Blue' is a new herbaceous perennial suitable for use as a landscape and container plant.

The new invention arose from an ongoing controlled breeding program by the Inventor in Vleuten, The Netherlands. The objectives of the breeding program are to develop new cultivars of *Aster alpinus* with compact habits and double flowers.

'X Blue' was derived from a controlled cross made by the Inventor in May of 2010 between an unnamed and unpatented plant of *Aster alpinus* from the Inventor's breeding program, reference no. 1001-01, as the female parent and *Aster alpinus* 'Sabine' (not patented) as the male parent. 'X Blue' was selected in June of 2012 as a single unique plant amongst the resulting seedlings.

Asexual reproduction of the new cultivar was first accomplished by cuttings in Noordwijk, The Netherlands in August of 2012 under the direction of the Inventor. Asexual propagation by tissue culture using meristem tissue and stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'X Blue' as a new and unique cultivar of *Aster.*

1. 'X Blue' exhibits inflorescences that are fully double and purple-blue in color.
2. 'X Blue' exhibits a freely branching and compact plant habit.

The female parent of 'X Blue', reference no. 1001-01, differs from 'X Blue' in having semi-double flowers and in having a more floriferous blooming habit. The male parent of 'X Blue', 'Sabine', differs from 'X Blue' in a less compact plant habit with longer stems. 'X Blue' can also be compared to the to the co-pending *Aster* cultivars 'X Pink' and 'X White'. Both cultivars are similar to 'X Blue' in having double inflorescences. 'X Pink' differs from 'X Blue' in having less branching, longer stems, and inflorescences that are pink in color with disc florets that are slightly longer. 'X White' differs from 'X Blue' in having inflorescences that are white in color and in having disc florets that are longer.

BRIEF DESCRIPTION OF THE DRAWINGS

The accompanying colored photographs illustrate the overall appearance and distinct characteristics of the new cultivar. The photographs were taken of a plant 20 weeks in age grown in a 23-cm container (with 5 plugs) in an unheated greenhouse in Noordwijk, The Netherlands.

Figure 1:
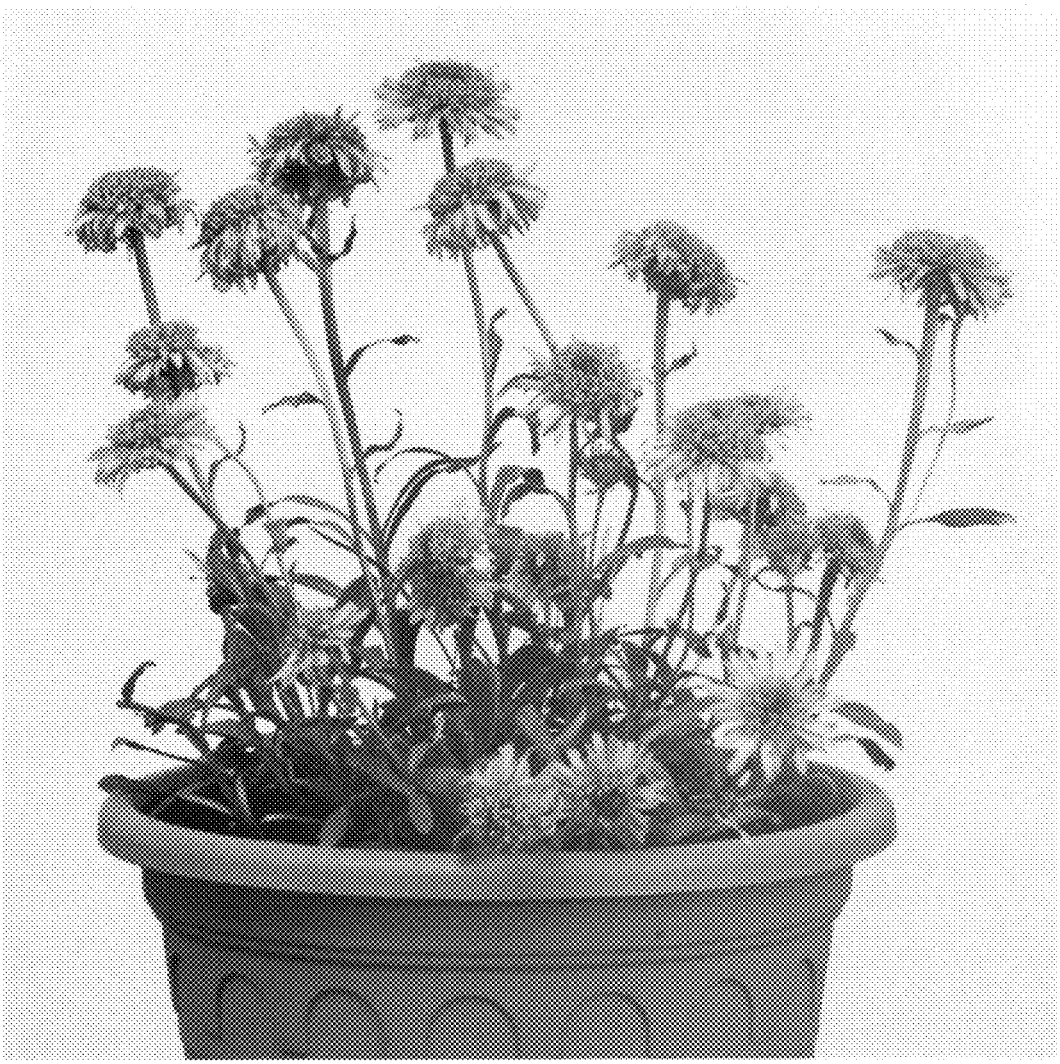
FIG. 1 provides a side view of the plant habit of 'X Blue' in bloom.
Figure 2:
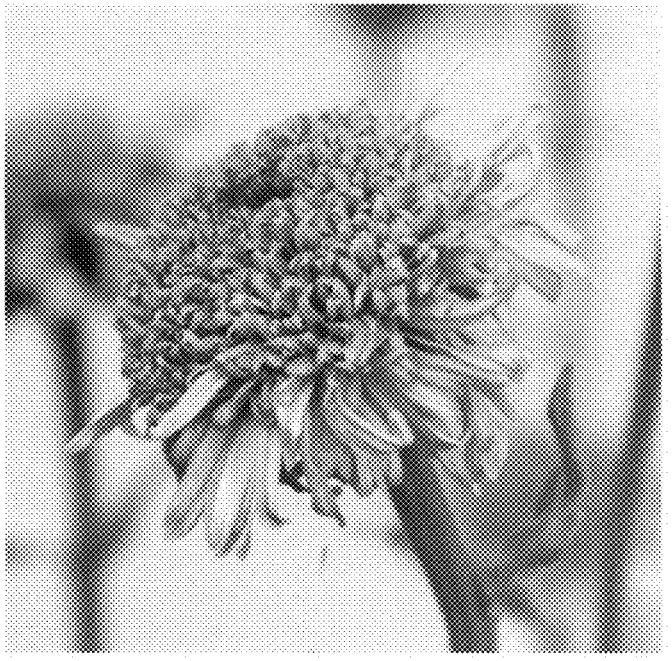
FIG. 2 provides a view of an inflorescence of 'X Blue'.
Figure 3:
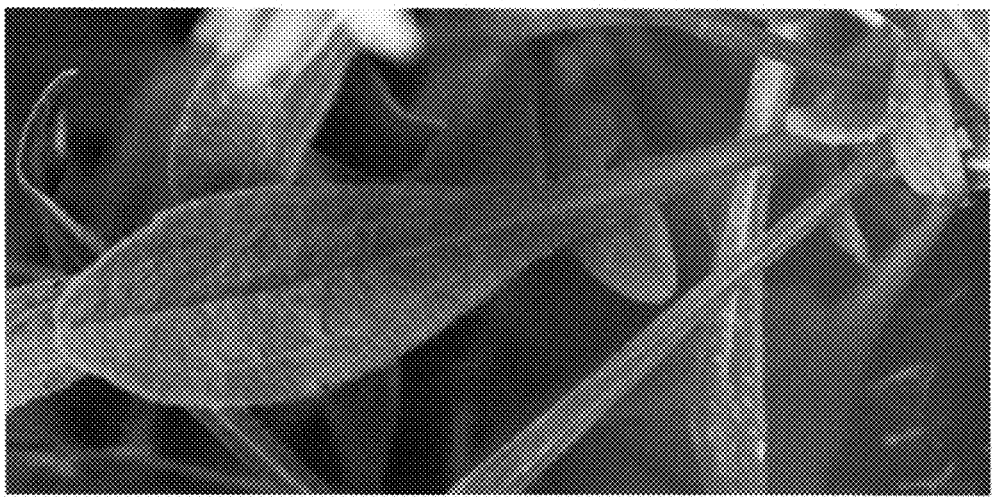
FIG. 3 provides a close-up view of the foliage of 'X Blue'.

The colors in the photographs are as close as possible with digital photography techniques available, the color values cited in the detailed botanical description accurately describe the colors of the new *Aster*.

DETAILED BOTANICAL DESCRIPTION

The following is a description of plants 20 weeks in age as grown in 23-cm containers (with 5 plugs) in an unheated greenhouse in Noordwijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season.*—From May to June in the Netherlands.

*Plant type.*—Herbaceous perennial.

*Plant habit.*—Freely branching and compact.

*Height and spread.*—Reaches a height of 25 cm and a spread of 30 cm.

*Cold hardiness.*—At least to U.S.D.A. Zone 4.

*Diseases resistance.*—No resistance or susceptibility to diseases has been observed.

*Root description.*—Fibrous and 158D in color.

*Root development.*—A rooted tissue culture plantlet will fully root in a 4-cm liner in 6 to 8 weeks.

*Propagation.*—Tissue culture from meristem tissue and stem cuttings.

*Growth rate.*—Moderate.

Stem description:

*Stem shape.*—Round.

*Stem color.*—138B to 138C.

*Stem surface.*—Moderately glossy and moderately covered with short soft adpressed hairs; an average of 0.5 mm and 155A in color.

*Stem size.*—12.4 cm in length and 2 mm in diameter.

*Stem aspect.*—Held at an average angle of 67.5° to soil level, varying between 45° and 90°.

*Branching habit.*—Average of 25 branches.

*Branch internode length.*—1.1 cm in length.

Foliage description:

*Leaf division.*—Simple.

*Leaf shape.*—Narrow oblanceolate.

*Leaf base.*—Long and narrow cuneate.

*Leaf apex.*—Obtuse.

*Leaf margin.*—Entire and moderately covered with very short strigose hairs; an average of 0.5 mm in length and NN155D in color.

*Internode length.*—Average of 1.1 cm.

*Leaf venation.*—Pinnate, upper surface 144B to 144C, lower surface 144A.

*Leaf attachment.*—Sessile.

*Leaf arrangement.*—Alternate.

*Leaf number.*—Average of 6 per stem.

*Leaf surface.*—Both surfaces slightly glossy, slightly rough to the touch and covered with very short hairs; an average of 0.3 mm in length and NN155D in color.

*Leaf color.*—Young upper surface; 144A, young lower surface; 143C, mature upper surface; 137A, mature lower surface; 138A.

*Leaf size (mature).*—Average of 5.7 cm in length and 1 cm in width.

*Leaf fragrance.*—None.

Flower description:

*Inflorescence type.*—Capitulum, 1 per stem.

*Lastingness of individual capitulum.*—Temperature dependent, typically last about 4 to 5 weeks.

*Fragrance.*—Faint and slightly musky.

*Quantity of capitulum.*—An average of 25 per plant.

*Capitulum buds.*—Average of 1.2 cm in length and diameter, broad elliptic in shape, color; 144B, top N82C, surface is glabrous with base pubescent.

*Capitulum size.*—About 4.7 cm in diameter and 2.7 cm in depth, diameter of disk about 3.1 mm.

*Peduncle.*—Terminal peduncle held straight on top of stem, moderate strength, 6.2 cm in length and 3 mm in width, densely covered with short soft adpressed hairs; an average of 0.5 mm in length and 155A in color, 138A to 138B in color.

*Involucral bracts.*—Average of 40 per inflorescence, placed spirally in two rows, lanceolate, twisted with entire and undulate margins, acute apex, cuneate base, 1 cm in length and 0.15 mm in width, upper and lower surface covered with very short pubescence 0.3 mm in length and NN155A in color, upper surface color; 138B to 138C, lower surface color; 143B.

Ray florets (carpellate):

*Number.*—Average of 93 per inflorescence.

*Shape.*—Oblanceolate.

*Aspect.*—Horizontal to downward when they mature.

*Size.*—Average of 2.1 cm in length and 3 mm in width.

*Apex.*—Broadly acute.

*Base.*—Cuneate.

*Margins.*—Entire.

*Surface.*—Both sides glabrous, upper side matte and velvety, lower side slightly glossy, base is covered with an average of 25 hairs; 5 mm in length and 157C to 157D in color.

*Color.*—When opening upper surface; N82B to N82C, when opening lower surface; N82C, when fully open upper surface; N82B, when fully open lower surface; N82C.

Disk florets (perfect):

*Quantity.*—Average of 230 per inflorescence.

*Shape.*—Tubular with an average of 4 free tips, spirally placed on disc held along the margin of the disc with the lower 45% fused into a tube, disc florets in the center of the disc with the lower 85% fused into a tube.

*Surface.*—Both surfaces glabrous and glossy, base is covered with an average of 25 hairs, 5 mm in length and 157C to 157D in color.

*Margin.*—Entire.

*Size.*—About 1.3 cm in length and 5 mm in width.

*Color.*—When opening and fully open upper surface; N82B, base 150C, when opening upper and lower surface; N82C, base 150C.

Reproductive organs:

*Presence.*—Disk florets are perfect, ray florets are carpellate.

*Gynoecium.*—1 pistil, style is 3.5 mm in length and 145D in color, ovary is 145B.

*Androecium.*—5 stamens per disk floret, anther is linear in shape, 13A in color and 2 mm in length, filament is 4 mm in length and 145D in color, pollen quantity is low and 12A in color.

*Fruit and seed.*—None observed to date.

It is claimed:

1. A new and distinct cultivar of *Aster* plant named 'X Blue' as described and illustrated herein.

* * * * *